United States Patent
Ikeda et al.

(10) Patent No.: US 6,559,268 B1
(45) Date of Patent: May 6, 2003

(54) PERFLUORO GROUP-CONTAINING COMPOUNDS AND HARDENED POLYMER OF THE SAME

(75) Inventors: Junichi Ikeda, Nara (JP); Hajimu Kawa, Austin, TX (US)

(73) Assignee: Kyoeisha Chemcial Co., Ltd. (JP)

( * ) Notice: Subject to any disclaimer, the term of this patent is extended or adjusted under 35 U.S.C. 154(b) by 0 days.

(21) Appl. No.: 09/527,288

(22) Filed: Mar. 17, 2000

(30) Foreign Application Priority Data

Mar. 17, 1999 (JP) ............................................ 11-072719

(51) Int. Cl.$^7$ ...................... C08G 59/68; C07D 303/12; C08F 283/00; C07C 69/52; C07C 41/00
(52) U.S. Cl. ........................... 528/88; 528/90; 549/554; 549/555; 549/556; 549/559; 549/561; 525/527; 525/403; 525/481; 560/209; 560/220; 560/223; 568/669; 568/685; 526/247; 526/245
(58) Field of Search .................. 549/554, 555, 549/556, 561, 559; 528/88, 90; 525/527, 403, 481; 560/209, 220, 223; 568/669, 685; 526/247, 245

(56) References Cited

U.S. PATENT DOCUMENTS 3,706,772 A * 12/1972 Reines ........................ 549/555
5,043,747 A * 8/1991 Ebisawa ..................... 549/559

FOREIGN PATENT DOCUMENTS

| DE | 29 39 550 A1 | 4/1980 |
| DE | 195 41 788 A1 | 5/1997 |
| EP | 0 219 928 A2 | 4/1987 |
| EP | 0 271 872 A2 | 6/1988 |
| EP | 0 599 023 A2 | 6/1994 |
| WO | WO 91/18859 | 12/1991 |
| WO | WO 98/12163 | 3/1998 |

OTHER PUBLICATIONS

Bassilana et al., "Synthesis of new β–hydroxylated and β–carboxylated bisquaternary ammonium salts containing fluorinated spacer groups," Journal of Fluorine Chemistry 92, 1998, pp. 109–117.

Bassilana et al., "Synthèse de nouveau diépoxides hautement fluorés, précurseurs de tensioactifs bolaphiles à espaceur fluor," Journal of Fluorine Chemistry 87, 1988, pp. 37–40.

* cited by examiner

*Primary Examiner*—Philip Tucker
(74) *Attorney, Agent, or Firm*—Parkhurst & Wendel, L.L.P.

(57) ABSTRACT

A perfluoro group-containing compound are represented by the following formula (I):

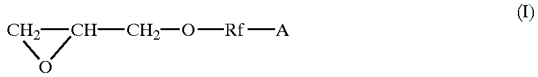

(I)

—Rf— is a perfluoro group; and —A represents —OH or a group:

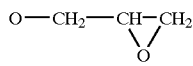

or $-C_yF_{2y+1}$ or $-C_zF_{2z-1}$ and a perfluoro group-containing polymerizable compound represented by the following formula (II):

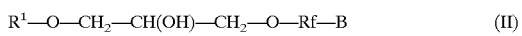

(II)

In Formula (II), —Rf— is a perfluoro group; —B is —OH or —O—CH$_2$—CH(OH)—CH$_2$—O—R$^2$, or —C$_y$F$_{2y+1}$ or —C$_z$F$_{2z-1}$; and R$^1$ and R$^2$ each is a dehydroxyl residue of a (meth)acryloyl group-containing compound or a vinyl group-containing compound. The hardened polymer from the compound has water-repellency, oil-repellency and adhering ability.

11 Claims, No Drawings

PERFLUORO GROUP-CONTAINING COMPOUNDS AND HARDENED POLYMER OF THE SAME

The present invention relates to a novel water-repellent and oil-repellent perfluoro group-containing compound and a hardened polymer thereof.

BACKGROUND OF THE INVENTION

The perfluoro group-containing compound is excellent in heat resistance because the linkages between carbon atoms and fluorine atoms are very strong and the compound has a low friction coefficient. For this reason, the perfluoro group-containing compound has been used for protecting the surface of a substrate by, for instance, applying it to the substrate surface; or incorporating it into a paint and applying the paint to the substrate surface to thus impart water repellency or oil repellency to the surface. For instance, Published International Patent Application No. WO98/12163 discloses a (meth)acrylic acid ester of perfluoro group-containing alcohol and a hardened polymer thereof and Japanese Patent Provisional Publication No. Hei 11-2702 discloses a low refractive index film comprising a perfluoro group-containing compound.

Under such circumstances, there has been desired for the development of a perfluoro group-containing compound and a hardened polymer thereof, whose adherence to the surface of a substrate is further improved.

SUMMARY OF THE INVENTION

Accordingly, it is an object of the present invention to provide a water-repellent and oil-repellent perfluoro group-containing novel, polymerizable compound.

It is another object of the present invention to provide a hardened polymer of the compound, whose adherence to the surface of a substrate is quite excellent.

The perfluoro group-containing compound of the present invention developed for accomplishing the foregoing objects is one represented by the following formula (I):

$$CH_2\text{---}CH\text{---}CH_2\text{---}O\text{---}Rf\text{---}A \quad (I)$$
$$\diagdown O \diagup$$

In Formula (I), —Rf— is a perfluoro group selected from the group consisting of —$CH_2$—$(CF_2)_m$—$(CH_2)_n$— (wherein m is an integer ranging from 1 to 20 and n is also an integer ranging from 0 to 1), —$CH_2$—$(CF_2)_p$—$C[$—$(CF_2)_q$—$F][$—$(CF_2)_r$—$F]$—$CH_2$— (wherein p is an integer ranging from 1 to 10, q is an integer ranging from 0 to 22 and r is an integer ranging from 1 to 22), —$CH_2$—$(CF_2)_s$—$($—$O$—$C_tF_{2t})_u$—$O$—$(CF_2)_v$—$(CH_2)_w$— (wherein s, t, u, v and w are integers ranging from 1 to 3, 1 to 4, 1 to 100, 0 to 3 and 0 to 1, respectively),

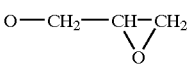

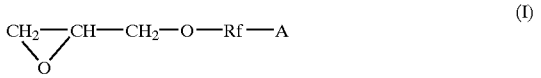

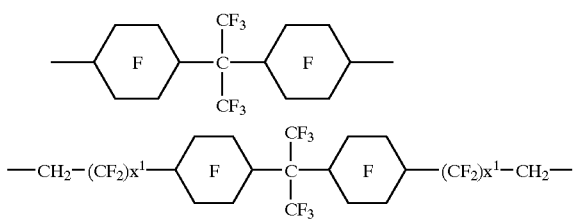

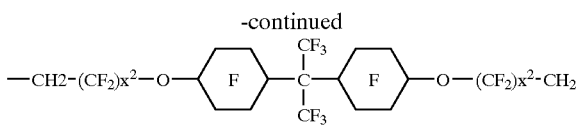

(wherein $x^1$ and $x^2$ each is an integer ranging from 0 to 10);
—A represents —OH or a group:

$$O\text{---}CH_2\text{---}CH\text{---}CH_2$$
$$\diagdown O \diagup$$

when n, v and w of the foregoing —Rf— not 0, or —$C_yF_{2y+1}$ (y is an integer ranging from 1 to 22) when m=1~3 and n=1, m+y=6~22 and n=0, v=w=0, in the foregoing group: —Rf—, or —$C_zF_{2z-1}$ (z is an integer ranging from 3 to 20) when m=1~10 and n=0, v=w=0 in the foregoing group: —Rf—.

The foregoing group: —$CH_2$—$(CF_2)_m$—$(CH_2)_n$— may be, for instance, a dehydrogenated residue of 2,2-difluoropropane diol, 2,2,3,3-tetrafluorobutane diol, 2,2,3,3,4,4-hexafluoropentane diol, 2,2,3,3,4,4,5,5-octafluorohexane diol, 2,2,3,3,4,4,5,5,6,6-decafluoroheptane diol, 2,2,3,3,4,4,5,5,6,6,7,7-dodecafluorooctane diol, 2,2,3,3,4,4,5,5,6,6,7,7,8,8-tetradecafluorononane diol or 2,2,3,3,4,4,5,5,6,6,7,7,8,8,9,9-heptadecafluorodecane diol, when n is not 0.

The foregoing group: —$CH_2$—$(CF_2)_p$—$C[$—$(CF_2)_q$—$F]$ $[$—$(CF_2)_r$—$F]$—$CH_2$— may be, for instance, a dehydrogenated residue of 2-fluoro-2-perfluorooctyl-1,3-propane diol, 2-fluoro-2-perfluoroisooctyl-1,3-propane diol or 2-fluoro-2-perfluoro (4-ethyl-hexyl)-2-hydroxymethyl-1-methanol.

The foregoing group: —$CH_2$—$(CF_2)_s$—$($—$O$—$C_tF_{2t})_u$—$O$—$(CF_2)_v$—$(CH_2)_w$— may be, for instance, a dehydrogenated residue of 2,2,4,4-tetrafluorodiethylene glycol, 2,2,4,4,5,5,7,7-octafluorotriethylene glycol, 2,2,4,4,5,5,7,7,8,8,10,10-dodecafluorotetraethylene glycol, 2,2,4,4,5,5,7,7,8,8,10,10,11,11,13,13-heptadecafluoro pentaethylene glycol, 2,2,4,4,5,5,7,7,8,8,10,10,11,11,13,13,14,14,16,16-eicosafluorohexaethylene glycol, 2,2,4,4,5,5,7,7,8,8,10,10,11,11,13,13,14,14,16,16,17,17,19,19-tetracosafluoroheptaethylene glycol, 2,2,4,4,5,5,7,7,8,8,10,10,11,11,13,13,14,14,16,16,17,17,19,19,20,20,22,22-octacosafluorooctaethylene glycol, 2,2,4,4,5,5,7,7,8,8,10,10,11,11,13,13,14,14,16,16,17,17,19,19,20,20,22,22,23,23,25,25-dotriacontafluorononaethylene glycol, 2,4,4-trifluoro-2,5-di(trifluoromethyl)diethylene glycol, 2,4,4,5,7,7-hexafluoro-2,5,8-tri(trifluoromethyl)triethylene glycol, 2,4,4,5,7,7,8,10,10-nonafluoro-2,5,8,11-tetra(trifluoromethyl) tetraethylene glycol, 2,4,4,5,7,7,8,10,10,11,13,13-dodecafluoro-2,5,8,11,14-penta(trifluoromethyl) pentaethylene glycol, 2,4,4,5,7,7,8,10,10,11,13,13,14,16,16-17-pentadecafluoro-2,5,8,11,14,17-hexa(trifluoromethyl) hexaethylene glycol, 2,4,4,5,7,7,8,10,10,11,13,13,14,16,16,17,19,19,20-octadecafluoro-2,5,8,11,14,17,20-hepta(trifluoromethyl)heptaethylene glycol, 2,4,4,5,7,7,8,10,10,11,13,13,14,16,16,17,19,19,20,22,22,23-docosafluoro-2,5,8,11,14,17,20,23-octa-(trifluoromethyl) octaethylene glycol, 2,4,4,5,7,7,8,10,10,11,13,13,14,16,16,17,19,19,20,22,22,23,25,25,26-tetracosafluoro-2,5,8,11,14,17,20,23,26-nona (trifluoromethyl)nonaethylene glycol, 2,2,3,3,4,4,6,6,7,7,8,8-dodecafluoroditetramethylene glycol, 2,2,3,3,4,4,6,6,7,7,8,8,9,9,11,11,12,12,13,13-eicosafluorotritetramethylene glycol, 2,2,3,3,4,4,6,6,7,7,8,8,9,9,11,11,12,12,13,13,14,14,16,16,17,17,18,18-octacosafluorotetratetramethylene glycol, 2,2-bis(4-hydroxy-decafluorocyclohexyl)-1,3-hexafluoropropane, 2,2-bis (4-hydroxymethyldecafluorocyclohexyl)-1,3-hexafluoropropane, 2,2-bis[4-oxy(1,1-difluoroethoxy)-decafluorocyclohexyl]-1,3-hexafluoropropane, or 2,2-bis[4-oxy(1-perfluoromethyl-1-fluoroethoxy)-decafluorocyclohexyl]-1,3-hexafluoropropane.

The group: $(C_yF_{2y+1})$—$CH_2O$— which constitutes the group: —$(C_yF_{2y+1})$, may be, for instance, a dehydrogenated residue of perfluoromethanol, perfluoroethyl methanol, perfluoropropyl methanol, perfluorobutyl methanol, perfluoropentyl methanol, perfluorohexyl methanol, perfluorooctyl methanol, perfluorononyl methanol, perfluorodecyl methanol, perfluoroundecyl methanol, perfluorododecyl methanol, perfluorotridecyl methanol, perfluorotetradecyl methanol, perfluoropentadecyl methanol, perfluorohexadecyl methanol, perfluoroheptadecyl methanol, perfluorooctadecyl methanol, perfluorononadecyl methanol, perfluoroeicosyl methanol, or perfluoroheneicosyl methanol. In addition, the group: $(C_yF_{2y+1})$—$OCF_2CH_2O$— may be, for instance, a dehydrogenated residue of 2-perfluoromethoxy-2,2-difluoroethanol, 2-perfluoroethoxy-2,2-difluoroethanol. The group: $(C_yF_{2y+1})$—$(CF_2CF_2$—$O$—$)_u$—$CF_2CH_2O$— may be, for instance, a dehydrogenated residue of 2-perfluorobutoxy-2,2-difluoroethanol, 2-perfluorooctoxy-2,2-difluoroethanol, 5-perfluoromethoxy-4,4,5,5-tetrafluoroethoxy-2,2-difluoroethanol, 5-perfluorobutoxy-4,4,5,5-tetrafluoroethoxy-2,2-difluoroethanol, 5-perfluorooctoxy-4,4,5,5-tetrafluoroethoxy-2,2-difluoroethanol, 8-perfluoromethoxy-7,7,8,8-tetrafluoroethoxy-4,4,5,5-tetrafluoroethoxy-2,2-difluoroethanol, 8-perfluorooctoxy-7,7,8,8-tetrafluoroethoxy-4,4,5,5-tetrafluoroethoxy-2,2-difluoroethanol, 11-perfluoromethoxy-10,10,11,11-tetrafluoroethoxy-7,7,8,8-tetrafluoroethoxy-4,4,5,5-tetrafluoroethoxy-2,2-difluoroethanol, or 11-perfluorooctoxy-10,10,11,11-tetrafluoroethoxy-7,7,8,8-tetrafluoroethoxy-4,4,5,5-tetrafluoroethoxy-2,2-difluoroethanol.

Examples of the group: $(C_zF_{2z-1})$—$CH_2O$— which constitutes the group: —$(C_zF_{2z-1})$— may be, for instance, a dehydrogenated residue of 1-undecafluorocyclohexyl methanol, 2-fluoro-2-undecafluorocyclohexyl ethanol, or 2,2,3-trifluoro-3-undecafluorocyclohexyl propanol.

A method for preparing a perfluoro group-containing epoxy compound represented by the foregoing formula (I) comprises the step of reacting a perfluoro group-containing mono- or di-alcohol with a halogenated epoxy propyl.

The perfluoro group-containing alcohol as a starting material can be prepared by, for instance, fluorinating a diester of an alkyl diol with fluorine gas in 1,1,2-trichlorotrifluoroethane and then reducing the fluorinated product with lithium aluminum hydride. The procedures for preparing the perfluoro group-containing alcohol will be described below while taking a di-alcohol (1) represented by the formula: HO—$CH_2$—Rf—$CH_2$—OH as an example of such an alcohol. As will be seen from the following reaction scheme (V):

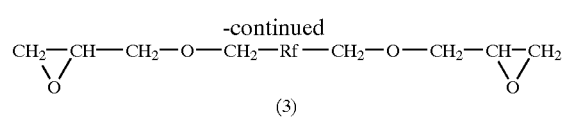

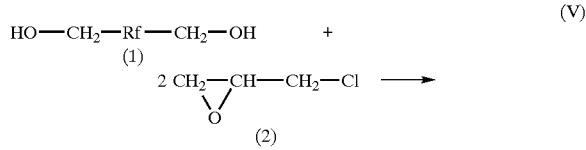

the alcohol reacts with a halogenated epoxy propyl (2) in the presence of a basic reagent to give a perfluoro group-containing epoxy compound (3). In this respect, the basic reagent may be, for instance, a metal hydroxide such as sodium hydroxide, potassium hydroxide, lithium hydroxide or calcium hydroxide; a metal alcoholate such as sodium methylate or potassium methylate; hydroxylamine; or tetraalkyl ammonium salt.

Alternatively, the perfluoro group-containing epoxy compound may likewise be prepared by reacting a perfluoro group-containing mono- or di-alcohol with a halogenated allyl and then oxidizing the reaction product with a peracid. Examples of such peracids are performic acid, peracetic acid, perpropionic acid, perbutyric acid, persuccinic acid, peradipic acid, pertrifluoroacetic acid, perbenzoic acid, monoperoxyphthalic acid, and p-nitro-perbenzoic acid.

The hardened polymer of the present invention is one obtained by polymerizing the perfluoro group-containing epoxy compound represented by the foregoing formula (I) using an amine, an acid anhydride, a polyamide resin, an imidazole, a mercaptan, a phenol, a Lewis acid-amine complex, or a photo-setting agent. Heating or irradiation with light rays can initiate the polymerization.

Examples of such amines are linear aliphatic polyamines such as diethylenetriamine, triethylenetetramine, tetraethylenepentamine and diethylaminopropylamine; alicyclic polyamines such as N-aminoethyl piperazine and isophorone-diamine; aromatic polyamines such as xylylenediamine, diamino-diphenyl methane and diamino-diphenyl sulfone; ethylene oxide or propylene oxide adducts of these polyamines; and modified amines such as cyanoethyl-modified polydmines and ketimine.

Examples of the foregoing acid anhydrides-are aromatic acid anhydrides such as phthalic anhydride, trimellitic anhydride and pyromellitic anhydride; and anhydrides of aliphatic acids such as maleic anhydride, succinic.anhydride, tetrahydrophthalic anhydride, methyl tetrahydrophthalic anhydride, methyl nadic anhydride, alkenyl succinic anhydride, hexahydrophthalic anhydride, methyl hexahydrophthalic anhydride and methyl-cyclohexene tetracarboxylic anhydride.

Examples of the foregoing polyamide resins are reaction products of dimeric acids or polycarboxylic acids with polyamines. Examples of the foregoing imidazoles are 2-methyl imidazole, 2-ethyl-4-methyl imidazole, 2-phenyl imidazole and combinations thereof with dicyan diamides. The foregoing mercaptans may be, for instance, liquid polymercaptans and polysulfide resins. Examples of phenols are novolak phenol, cresol novolak phenol and polyvinyl phenol.

Moreover, examples of the foregoing Lewis acid-amine complexes are complexes of Lewis acids such as boron trifluoride, phosphorus pentafluoride, arsenic pentafluoride and antimony pentafluoride with amines such as monoethylamine, benzylamine, piperidine, triethylamine and aniline. Examples of the foregoing photo-setting agents are aromatic diazonium Lewis acid salt, diallyl iodonium Lewis acid salt, triallylsulfonium Lewis acid salt and triallyl selenide.

The foregoing compounds can likewise be polymerized using other catalysts such as dicyan diamide, organic acid hydrazides, diaminomaleonitrile and derivatives thereof, melamine and derivatives thereof, amine imide and polyamine salts. Moreover, the catalyst may be those listed above absorbed on molecular sieve or encapsulated products of the foregoing catalysts. These catalysts may be used alone or in any combination.

The prepolymer according to the present invention is one obtained by the reaction of a perfluoro group-containing epoxy compound represented by the foregoing formula (I) with at least one member selected from the group consisting of amines, diols, dicarboxylic acids, acid anhydrides, polyamide resins, imidazoles, mercaptans, phenols, and Lewis acid-amine complexes and has a number average molecular weight ranging from $0.5 \times 10^3$ to $1 \times 10^6$.

Examples of amines, acid anhydrides, polyamides, imidazoles, mercaptans, phenols, and Lewis acid-amine complexes are the same as those listed above; examples of diols are alkyl diols and perfluoro group-containing dialcohols. Examples of dicarboxylic acids are the foregoing aromatic acids and aliphatic acids. It is also possible to use dicyan diamides, organic acid hydrazides, diaminomaleonitriles and derivatives thereof, melamine and derivatives thereof, amine imides, polyamine salts, or those listed above absorbed on molecular-sieve or encapsulated products of the foregoing catalysts.

The hardened polymers other than those listed above include the foregoing prepolymers, which are crosslinked with crosslinking agents such as polyisocyanates or acid anhydrides.

More specifically, hydroxyl groups are newly formed through the addition reaction of the epoxy groups of the perfluoro group-containing epoxy compound and diamines. These hydroxyl groups undergo addition reactions with the isocyanate groups of polyisocyanates to cause polymerization with crosslinking in a network structure and to thus cause hardening.

Examples of polyisocyanates are diisocyanates and triisocyanates such as toluene diisocyanate, diphenylmethane diisocyanate, xylylene diisocyanate, naphthalene diisocyanate, triphenylene triisocyanate, tris(isocyanate phenyl)thiophosphate, hexamethylene diisocyanate, methylene-bis(cyclohexyl diisocyanate), isophorone diisocyanate, trimethyl hexamethylene diisocyanate, bis (isocyanate methyl)cyclohexane and norbornene diisocyanate; adducts, buretes and isocyanurates derived from the foregoing diisocyanates, and block derivatives in which the isocyanate groups are protected with, for instance, phenols in order to impart storage stability to diisocyanates and which are dissociated into those carrying free isocyanate groups by heating prior to use.

The perfluoro group-containing polymerizable compounds of the present invention are those represented by the following formula (II):

$$R^1\!-\!O\!-\!CH_2\!-\!CH(OH)\!-\!CH_2\!-\!O\!-\!Rf\!-\!B \qquad (II)$$

In Formula (II), —Rf— is the same as that defined above in connection with Formula (I); —B is —OH or —O—CH$_2$CH (OH)—CH$_2$—O—R$^2$, or —C$_y$F$_{2y+1}$ or —C$_z$F$_{2z-1}$ (y and z are the same as those defined above); R$^1$ and R$^2$ each is a dehydroxyl residue of a (meth)acryloyl group-containing compound or a vinyl group-containing compound.

The perfluoro group-containing polymerizable compound represented by Formula (II) can be prepared by reacting the epoxy group of a perfluoro group-containing epoxy compound with the hydroxyl group of a (meth)acryloyl group-containing compound or a vinyl group-containing compound through the ring-opening addition reaction.

A specific example thereof will be described below while taking the reaction of a perfluoro group-containing epoxy compound (3) with acrylic acid (4) as a typical example. The reaction is shown in the following reaction scheme (VI):

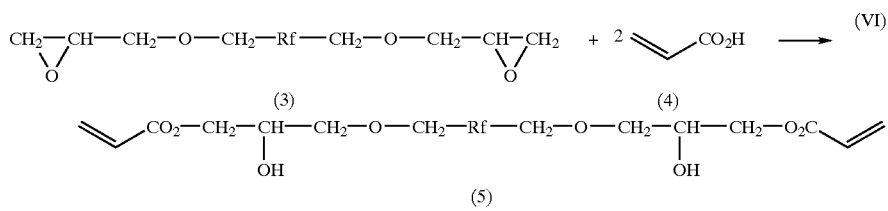

As will be seen from the reaction scheme (VI), the carboxyl group of the acrylic acid (4) is reacted with the epoxy group of the compound (3) through the ring-opening addition reaction in the presence of a basic reagent to give an acrylic acid diester (5). The basic reagent may be, for instance, tertiary amines such as dimethyl benzylamine; quaternary ammonium salts such as tetramethylammonium chloride; or phosphorus atom-containing compounds such as triphenyl phosphine.

Examples of (meth)acryloyl group-containing compounds include (meth)acrylic acid, (meth)acryloyloxy aliphatic acids, such as (meth)acryloyloxy propionic acid. These (meth)acryloyl group-containing compounds are reacted with epoxy compounds (3) through the ring-opening addition reaction to give polymerizable ester compounds.

Examples of vinyl group-containing compounds are allyl alcohol, hydroxyethyl vinyl ether, hydroxybutyl vinyl ether and monovinyl ether of cyclohexane dimethanol. These vinyl group-containing compounds are reacted with epoxy compounds (3) through the ring-opening addition reaction in the presence of a catalyst to form ether bonds and to thus give polymerizable compounds. As such catalysts, there may be listed, for instance, metal hydroxides such as sodium hydroxide, potassium hydroxide, lithium hydroxide and calcium hydroxide; metal alcoholates such as sodium methylate and potassium methylate; and boron trifluoride-ether complexes.

Alternatively, it is also possible to use acrylic acid monoesters such as those prepared by reacting halogenated epoxypropyl with only one terminal hydroxyl group of the dialcohol (1) or by reacting halogenated epoxypropyl with the hydroxyl group of a monoalcohol to give a monoether and then reacting the monoether with (meth)acryloyl group-containing compounds. It is also possible to use those obtained by reacting the monoether with vinyl group-containing compounds.

Prepolymers of the present invention other than those described above are ones formed by the polymerization of the unsaturated groups of the perfluoro group-containing compounds represented by the foregoing Formula (II) and having a number average molecular weight ranging from 0.5×10³ to 1×10⁶. The perfluoro group-containing polymerizable compound can be polymerized under the irradiation of light rays or in the presence of a heat polymerization initiator to give a prepolymer.

Another hardened polymer according to the present invention is one obtained by crosslinking the foregoing prepolymer with a crosslinking agent such as a polyisocyanate or an acid anhydride. Examples of such polyisocyanates or acid anhydrides usable herein are the same as those already listed above. The hardened polymer may likewise be one obtained by polymerization, with crosslinking, of the prepolymer through the unsaturated groups thereof.

More specifically, the hardened polymer may be prepared as follows: A perfluoro group-containing compound is reacted with a dialcohol to form a prepolymer. Then a solution containing the prepolymer and a diisocyanate is prepared, followed by applying the solution onto the surface of a substrate such as plastics, metals, wood, paper, glass and concrete, and then heating the resulting film or irradiating it with visible light rays or ultraviolet rays. The unsaturated groups present in the polymerizable compounds are polymerized with crosslinking and thus hardened in a network structure to thus form a hardened polymer.

Alternatively, such a coated film may be those obtained by applying a polymerizable compound-containing paint or ink onto the surface of such a substrate.

DETAILED DESCRIPTION OF THE INVENTION

The perfluoro groups present in the hardened polymer are linked to unsaturated groups through ether bonds originated from epoxy propyl ether and therefore, they have high degree of freedom and a high migration ability. The perfluoro groups does not inhibit the exposure, on the molecular surface, of polar groups such as hydroxyl, ether and ester groups generated through the opening of the epoxy rings. For this reason, when the perfluoro group-containing polymerizable compound is polymerized on the surface of a substrate, the hardened polymer shows excellent adhesion to the interface of a substrate through the interaction between the polar groups of the polymer and those present on the surface. If the perfluoro group has a ring-like structure or it is in a branched state, the degree of its freedom is further enhanced and therefore, the adhesion between the polymer and the substrate is in turn further improved.

These hardened polymers are firmly adhered to the substrate surface and therefore, they are not easily separated from the surface. Moreover, the perfluoro groups of the polymer are exposed on the surface to thus reduce the interface energy of the substrate and accordingly, the surface of the substrate is excellent in the water-repellency and oil-repellency. The hardened polymer may be used as a coated film for protecting the substrate and/or an antireflecting film for the substrate.

The present invention will be described in more detail below with reference to the following Examples, but the present invention is not restricted to these specific Examples at all.

Specifically, the perfluoro group-containing epoxy compound and the hardened polymer thereof according to the present invention can be prepared according to the following methods.

EXAMPLE 1

To a 300 ml volume 4-necked flask equipped with a condenser, a stirring machine and a dropping device, there were added 20.0 g of 2-fluoro-2-perfluorooctyl-1,3-propane-diol, 72.2 g of epichlorhydrin and 0.2 g of tetramethylammonium chloride and then the content of the flask was heated to 100° C. with stirring. Further a 20% sodium hydroxide aqueous solution was dropwise added to the resulting mixture at that temperature to thus react them for 2 hours with stirring. The reaction system was dissolved in toluene, the toluene solution was neutralized with a 1% sodium primary phosphate solution and concentrated under reduced pressure. The resulting concentrate was filtered to give 14.3 g of an oligomer or a perfluoro group-containing epoxy compound (epoxy equivalent, i.e., the molecular weight divided by the number of epoxy groups present in the molecule: 744) as a yellow viscous liquid having a refractive index of 1.3720 as determined at 20° C. using an Abbe's refractometer (available from ATAGO Company). The resulting oligomer was analyzed by the $^{19}$F-nuclear magnetic resonance technique and it was found that the peak originated from the CF group at 2-position was shifted to the high magnetic field side by about 2 ppm. In addition, it was subjected to the infrared (IR) absorption spectroscopy and it was found that there was observed a peak originated from the epoxy group at about 850 cm$^{-1}$. Thus, the structure of the oligomer could clearly be confirmed.

To a 300 ml volume 4-necked flask equipped with a condenser, a stirring machine and a dropping device, there were added 10.0 g of this oligomer, 20.0 g of 2-fluoro-2-perfluorooctyl-1,3-propane-diol, 0.1 g of fine particulate sodium hydroxide and 50 g of methyl isobutyl ketone, followed by heating the resulting mixture at 100° C. for 3 days with stirring, neutralization thereof with a sodium primary phosphate aqueous solution, water-washing and concentration of the mixture to give a prepolymer. The prepolymer was found to have an epoxy equivalent of 7209, a hydroxyl equivalent or the value of the molecular weight divided by the number of hydroxyl groups present in the molecule of 310, a polystyrene-reduced weight-average molecular weight, as determined by the gel permeation chromatography (GPC) of 1,625 and a number-average molecular weight, as determined by the same technique, of 1,349.

Then a sample liquid (a) was prepared by mixing 1.86 g of a 16.7% tetrahydrofuran (THF) solution of this prepolymer, 1.70 g of a 10% THF solution of trimer of hexamethylene diisocyanate and 0.04 g of a 10% THF solution of dibutyl tin dilaurate at room temperature. The sample liquid was used in the adhesion test and for the determination of the contact angle with respect to water.

(1) Adhesion Test (Japanese Industrial Standards K-6850-1994)

The sample liquid (a) was applied onto the surface of two aluminum plates, which had been treated, in advance, with 1.2 to 1.5 mil of an epoxy primer in an area having a size of 12.5×12.5 mm, followed by drying the coated layer at 60° C. for 2 minutes, then bonding these plates together, and polymerization of the layers by heating them at 140° C. for 30 minutes to thus form a hardened polymer. The hardened polymer was allowed to stand at 25° C. for 24 hours and the tensile shear strength thereof was determined using an autograph (AGS-D) available from Shimadzu Corporation at a speed of 50 mm/min. As a result, the tensile shear strength was found to be 230 kgf/cm³ (separation at the aluminum-primer boundary).

(2) Determination of Contact Angle with Respect to Water

The sample liquid (a) was applied onto the surface of a glass plate, followed by polymerization of the sample liquid by heating it to 140° C. for 30 minutes to give a hardened polymer. After cooling the plate, 0.1 ml of ion-exchanged water was placed on the surface of the plate to thus determine the contact angle. It was found to be 111°.

Further, a sample liquid (b) was prepared by repeating the same procedures used for preparing the sample liquid (a) except that 2.1 g of a 10% THF solution of norbornene diisocyanate was substituted for the THF solution of trimer of hexamethylene diisocyanate. The resulting sample liquid (b) was subjected to the test for weatherability.

(3) Test for Weatherability

A hardened polymer was prepared by repeating the same procedures used in (2) (determination of contact angle with respect to water) except for using the sample liquid (b) in place of the sample liquid (a). The glass plate was irradiated, for 24 hours, with light rays from a UV lamp of 100 mW/cm$^3$ using a measurement equipment Super UV: SUV-W131 (available from Iwasaki Electric Co., Ltd.) at a black panel temperature of 70° C. and a humidity of 50%. Ion-exchanged water was sprayed on the glass plate for one minute in intervals of one hour, during the light-irradiation step. The contact angles observed before and after the irradiation were found to be 105° and any change was not detected.

EXAMPLE 2

To a 200 ml volume 4-necked flask equipped with a condenser, a stirring machine and a dropping device, there were added 10 g of perfluorooctyl methanol, 50 g of epichlorhydrin and 0.2 g of tetramethylammonium chloride, followed by heating the content of the flask to 80° C. with stirring. Further 1.8 g of a 50% sodium hydroxide aqueous solution was dropwise added to the flask at that temperature to thus react them for 2 hours. The reaction liquid was neutralized with a 1% sodium primary phosphate solution and then concentrated under reduced pressure. The concentrate was filtered to give 14.8 g of a perfluoro group-containing epoxy compound as a pale yellow liquid (epoxy equivalent: 510) having a refractive index of 1.3400 as determined at 25° C. using Abbe's refractometer (available from ADACO Company). The structure of this epoxy compound was confirmed by the fact that when the compound was analyzed by the IR absorption spectroscopy, an absorption peak originated from the epoxy group could be observed at about 850 cm$^{-1}$.

To a 200 ml volume 4-necked flask equipped with a condenser, a stirring machine and a dropping device, there were added 5.1 g of this epoxy compound, 0.2 g of tetramethylammonium chloride and 0.05 g of p-methoxy phenol, followed by heating the content of the flask at 80° C. with stirring. Further 0.72 g of acrylic acid was dropwise added to the content of the flask at that temperature and the resulting mixture was stirred for additional 24 hours. To the resulting reaction liquid, there was added 50 ml of toluene, followed by neutralization thereof with a 1% sodium bicarbonate aqueous solution, washing with a saturated common salt aqueous solution, concentration of the mixture and filtration thereof to give a perfluoro group-containing polymerizable compound or an acrylic acid ester. This acrylic acid ester was subjected to the IR absorption spectroscopic measurement. As a result, any absorption peak at about 850 cm$^{-1}$ originated from the epoxy group was not observed at all, an absorption attributable to the ester bond was detected near 1700 cm$^{-1}$ and an absorption peak attributable to the hydroxyl group was observed near 3000 cm$^{-1}$. These facts would clearly confirm the structure of the acrylic acid ester. In addition, the GPC analysis showed a peak at a polystyrene-reduced number-average molecular weight of about 600. The refractive index of the resulting acrylic acid ester was found to be 1.3640 as determined at 25° C. using Abbe's refractometer.

The acrylic acid ester to which 3% of 1-phenyl-2-hydroxy-2-methylpropan-1-one had been added was applied onto the surface of an aluminum plate in a thickness of 30 μm, the coated layer was covered with a releasing PET film, followed by mounting the aluminum plate on a conveyer moving at a velocity of 6 m/min, repeating three times the irradiation of the plate with light rays from a 1 kW high pressure mercury lamp (80 W/cm) arranged at a height of 10 cm to polymerize the coated layer with crosslinking by the action of the ultraviolet rays and to thus give a hardened polymer. The contact angle between the hardened polymer and water was found to be 110°. In addition, the pencil hardness thereof was found to be 2 B. Moreover, the glass transition point (Tg) thereof as determined by the measurement of the visco elasticity was found to be 20° C.

EXAMPLE 3

A perfluoro group-containing epoxy compound and an acrylic acid ester were prepared by repeating the same procedures used in Example 2 except that 10 g of perfluorocyclohexyl propanol was substituted for the same amount of the perfluorooctyl methanol used in Example 2 and that the amount of the 50% sodium hydroxide aqueous solution was changed to 2.2 g. This epoxy compound had an epoxy equivalent of 540. When the epoxy compound was analyzed by the IR absorption spectroscopy, it was found that a peak originated from the epoxy group was observed at about 850 cm$^{-1}$ and thus the structure of the compound was clearly confirmed by this fact. In addition, the acrylic acid ester was subjected to the IR absorption spectrometric analysis and it was found that any absorption peak at about 850 cm$^{-1}$ originated from the epoxy group was not observed at all, the ester showed a peak attributable to the epoxy bond near 1700 cm$^{-1}$ and a peak attributable to the hydroxyl group near 3000 cm$^{-1}$. Thus, the structure of the ester could be confirmed by these facts. The acrylic acid ester showed a peak in the GPC analysis at a polystyrene-reduced number-average molecular weight of about 500. The refractive index of the acrylic acid ester was found to be 1.3620 as determined at 25° C. using Abbe's refractometer.

The acrylic acid ester to which 3% of 1-phenyl-2-hydroxy-2-methylpropan-1-one had been added was applied onto the surface of an aluminum plate in a thickness of 30 μm, the coated layer was covered with a releasing PET film, followed by mounting the aluminum plate on a conveyer moving at a velocity of 6 m/min, repeating three times the irradiation of the plate with light rays from a 1 kW high pressure mercury lamp (80 W/cm) arranged at a height of 10 cm to polymerize the coated layer with crosslinking by the irradiation thereof with ultraviolet rays and to thus give a hardened polymer. The contact angle between the hardened polymer and water was found to be 110°. In addition, the pencil hardness thereof was found to be H. Moreover, the glass transition point (Tg) thereof as determined by the measurement of the visco elasticity was found to be 20° C.

EXAMPLE 4

A perfluoro group-containing epoxy compound and an acrylic acid ester were prepared by repeating the same procedures used in Example 2 except that 10 g of 2,2,3,3, 4,4,6,6,7,7,8,8,9,9,11,11,12,12,13,13-eicosafluoro-tri (tetramethylene glycol) was substituted for the same amount of the perfluorooctyl methanol used in Example 2, that the amount of the 50% sodium hydroxide aqueous solution was changed to 2.8 g and that the amount of acrylic acid used was changed to 1.86 g. This epoxy compound had an epoxy equivalent of wpe 387. The compound was subjected to the IR absorption spectroscopic analysis and it was found that a peak attributable to the epoxy group was observed at around 850 cm$^{-1}$. The structure of the epoxy compound could thus be confirmed. On the other hand, the acrylic acid ester was likewise subjected to the IR absorption spectroscopy. As a result, there was not observed any peak at around 850 cm$^{-1}$ attributable to the epoxy group, while there were observed a peak attributable to the ester bond at about 1700 cm$^{-1}$ and a peak attributable to the hydroxyl.group near 3000 cm$^{-1}$. The structure of the acrylic acid ester could thus be confirmed. The acrylic acid ester showed a peak in the GPC analysis at a polystyrene-reduced number-average molecular weight of about 500. The refractive index of the acrylic acid ester was found to be 1.3700 as determined at 250° C. using Abbe's refractometer.

The acrylic acid ester to which 3% of 1-phenyl-2-hydroxy-2-methylpropan-1-one had been added was applied onto the surface of an aluminum plate in a thickness of 30 μm, the coated layer was covered with a releasing PET film, followed by mounting the aluminum plate on a conveyer moving at a velocity of 6 m/min, repeating three times the irradiation of the plate with light rays from a 1 kW high pressure mercury lamp (80 W/cm) arranged at a height of 10 cm to polymerize the coated layer with crosslinking by the irradiation thereof with ultraviolet rays and to thus give a hardened polymer. The contact angle between the hardened polymer and water was found to be 92°. In addition, the pencil hardness thereof was found to be 2 B.

As has been described above in detail, a novel perfluoro group-containing polymerizable compound can be prepared using the perfluoro group-containing epoxy compound according to the present invention. The hardened polymer prepared from the perfluoro group-containing polymerizable compound has water-repellency and oil-repellency. The hardened polymer can firmly and stable adhered to the surface of a substrate and therefore, the polymer permits the protection of the substrate from any attacks of moisture and oils over a long period of time.

What is claimed is:

1. A perfluoro group-containing epoxy compound of the formula

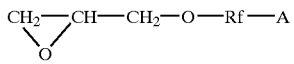

wherein —A is a member selected from the group consisting of —OH,

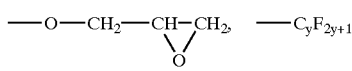

where y is an integer from 1 to 22, and —C$_z$F$_{2z-1}$ where z is an integer from 3 to 20, with the provisos that (1) when —A is —OH or —C$_z$F$_{2z-1}$, —Rf— is a perfluoro group selected from the group consisting of
—CH$_2$—(CF$_2$)$_m$—(CH$_2$)$_n$— where m is an integer from 1 to 20 and n is 0 or 1,
—CH$_2$—(CF$_2$)$_p$—C[—(CF$_2$)$_q$—F][(CF$_2$)$_r$—F]—CH$_2$— where p is an integer from 1 to 10, q is an integer from 0 to 22, and r is an integer from 1 to 22,
—CH$_2$—(CF$_2$)$_s$—(O—C$_t$F$_{2t}$)$_u$—O—(CF$_2$)$_v$—(CH$_2$)$_w$— where s is an integer from 1 to 3, t is an integer from 1 to 4, u is an integer from 1 to 100, v is an integer from 0 to 3, and w is 0 or 1,

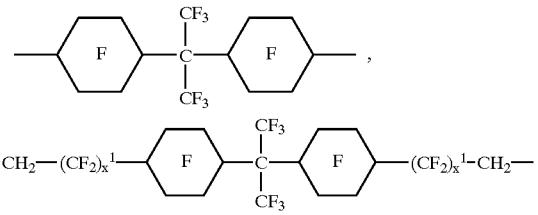

is a perfluoro-cyclohexyl group,

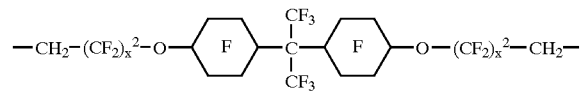

where x$^1$ is an integer from 0 to 10 and

is a perfluoro-cyclohexyl group,

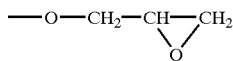

where x$^2$ is an integer from 0 to 10 and

is a perfluoro-cyclohexyl group; and (2) when —A is

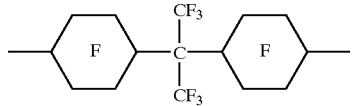

or —C$_y$F$_{2y+1}$, —Rf— is a perfluoroalkyl group selected from the group consisting of —CH$_2$—(CF$_2$)$_s$—(O—C$_t$F$_{2t}$)$_u$—O—(CF$_2$)$_v$—(CH$_2$)$_w$—,

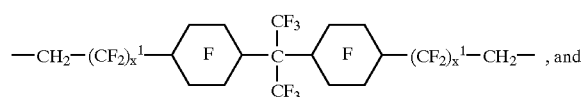

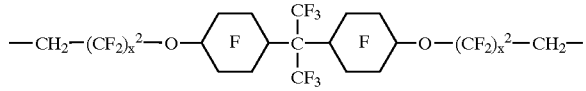

where s, t, u, v, w, and

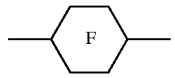

are as defined above.

2. A method for preparing the perfluoro group-containing epoxy compound of claim 1 comprising reacting a perfluoro group-containing mono- or di-alcohol with a halogenated epoxy propyl.

3. A method for preparing the perfluoro group-containing epoxy compound of claim 1 comprising reacting a perfluoro group-containing mono- or di-alcohol with a halogenated allyl compound to form a reaction product and then oxidizing the reaction product with a peracid.

4. A hardened polymer that is a polymer obtained by polymerizing the perfluoro group-containing epoxy compound of claim 1 in the presence of amines, acid anhydrides, polyamide resins, imidazoles, mercaptans, phenols, Lewis acid-amine complexes, or photo-setting agents.

5. A prepolymer that is a reaction product of the perfluoro group-containing epoxy compound of claim 1 and at least one member selected from the group consisting of amines, diols, dicarboxylic acids, acid anhydrides, polyamides, imidazoles, mercaptans, phenols, and Lewis acid-amine complexes, the prepolymer having a number-average molecular weight ranging from $0.5 \times 10^3$ to $1 \times 10^6$.

6. A hardened polymer obtained by crosslinking the prepolymer of claim 5 with a crosslinking agent selected from the group consisting of a polyisocyanate and an acid anhydride.

7. A perfluoro group-containing polymerizable compound of the formula $R^1$—O—$CH_2$—CH(OH)—$CH_2$—O—Rf—B wherein —Rf— is a perfluoro group selected from the group consisting of —$CH_2$—$(CF_2)_m$—$(CH_2)_n$— where m is an integer from 1 to 20 and n is 0 or 1,
—$CH_2$—$(CF_2)_p$—C[—$(CF_2)_q$—F][—$(CF_2)_r$—F]—$CH_2$— where p is an integer from 1 to 10, q is an integer from 0 to 22, and r is an integer from 1 to 22,
—$CH_2$—$(CF_2)_s$—(O—$C_tF_{2t}$)$_u$—O—$(CF_2)_v$—$(CH_2)_w$— where s is an integer from 1 to 3, t is an integer from 1 to 4, u is an integer from 1 to 100, v is an integer from 0 to 3, and w is 0 or 1,

,

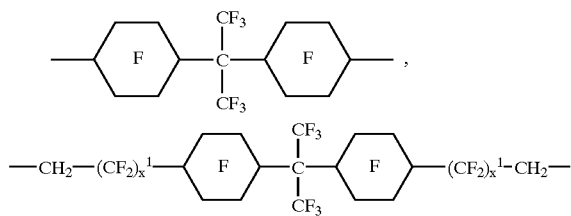

where $x^1$ is an integer from 0 to 10 and

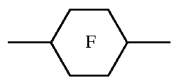

is a perfluoro-cyclohexyl group,

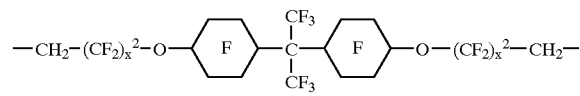

where $x^2$ is an integer from 0 to 10 and

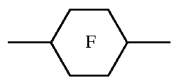

is a perfluoro-cyclohexyl group; —B is —OH, —O—$CH_2$—CH(OH)—$CH_2$—O—$R^2$, —$C_yF_{2y+1}$ where y is an integer from 1 to 22, or —$C_zF_{2z-1}$ where z is an integer from 3 to 20; and $R^1$— and —$R^2$ are each a dehydroxyl residue of a (meth)acryloyl group-containing compound or a vinyl group-containing compound.

8. A method for preparing the perfluoro group-containing polymerizable compound of claim 7 comprising reacting the epoxy ring of a perfluoro group-containing epoxy compound of the formula

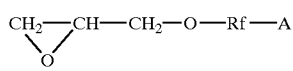

where —A is a member selected from the group consisting of —OH,

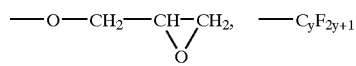

where y is an integer from 1 to 22, and —$C_zF_{2z-1}$ where z is an integer from 3 to 20, with the hydroxyl group of a (meth) acryloyl group-containing compound or a vinyl group-containing compound through a ring-opening addition reaction.

9. A prepolymer obtained by polymerizing the unsaturated group of a perfluoro group-containing polymerizable compound represented of the formula $R^1$—O—$CH_2$—CH(OH)—$CH_2$—O—Rf—B of claim 7, the prepolymer having a number-average molecular weight ranging from $0.5 \times 10^3$ to $1 \times 10^6$.

10. A hardened polymer obtained by crosslinking the prepolymer of claim 9, with a crosslinking agent selected from the group consisting of a polyisocyanate and an acid anhydride.

11. A hardened polymer obtained by polymerization, with crosslinking, through unsaturated groups of a prepolymer of claim 9.

* * * * *

UNITED STATES PATENT AND TRADEMARK OFFICE
CERTIFICATE OF CORRECTION

PATENT NO. : 6,559,268 B1
DATED : May 6, 2003
INVENTOR(S) : Junichi Ikeda et al.

It is certified that error appears in the above-identified patent and that said Letters Patent is hereby corrected as shown below:

<u>Title page,</u>
Item [73], Assignee, change "Kyoeisha Chemcial Co., Ltd." to
-- Kyoeisha Chemical Co., Ltd. --.

Signed and Sealed this

First Day of July, 2003

JAMES E. ROGAN
*Director of the United States Patent and Trademark Office*